United States Patent [19]

Duthie, Jr.

[11] Patent Number: 5,547,635
[45] Date of Patent: Aug. 20, 1996

[54] STERILIZATION METHOD AND APPARATUS

[76] Inventor: Robert E. Duthie, Jr., 9321 Warner Gulf Rd., Holland, N.Y. 14080

[21] Appl. No.: 150,280

[22] Filed: Nov. 10, 1993

Related U.S. Application Data

[63] Continuation of Ser. No. 816,853, Jan. 2, 1992, abandoned, which is a continuation of Ser. No. 257,444, Oct. 17, 1988, abandoned, which is a continuation-in-part of Ser. No. 112,504, Oct. 22, 1987, abandoned.

[51] Int. Cl.$^6$ ................................................ A61L 2/00
[52] U.S. Cl. .................. 422/24; 250/455.11; 422/22; 422/186.05; 422/186.3
[58] Field of Search .................. 422/22, 24, 121, 422/186.05, 186.3; 250/493, 455.11

[56] References Cited

U.S. PATENT DOCUMENTS

| | | | |
|---|---|---|---|
| 2,452,201 | 10/1948 | Levinson et al. | 422/24 |
| 2,681,061 | 6/1954 | Modell | 250/504 |
| 3,353,905 | 11/1967 | Ellis | 422/291 |
| 3,447,892 | 6/1969 | Watson et al. | 422/291 |
| 3,654,108 | 4/1972 | Smith, Jr. | 204/164 |
| 3,674,421 | 7/1972 | Decupper | 422/121 |
| 3,769,517 | 10/1973 | Coleman . | |
| 3,852,032 | 12/1974 | Urbach | 422/24 |
| 3,906,236 | 9/1975 | Callahan | 250/455 |
| 3,955,922 | 5/1976 | Moulthrop | 422/300 |
| 4,182,665 | 1/1980 | Mibu et al. | 204/159.15 |
| 4,276,479 | 6/1981 | Mibu et al. | 250/492 R |
| 4,298,005 | 11/1981 | Mutzhas | 128/396 |
| 4,424,188 | 1/1984 | DiGeronimo | 422/20 |
| 4,534,282 | 8/1985 | Marinoza | 99/451 |

FOREIGN PATENT DOCUMENTS

| | | |
|---|---|---|
| 8603414 | 6/1986 | Japan . |
| 2175777 | 12/1986 | United Kingdom . |

OTHER PUBLICATIONS

Disinfecting Air With Sterilizing Lamps, Nagy et al, pp. 82–87, Heating, Piping & Air Conditioning, vol. 26, Nos. 1–12, 1954.

Advances in Sterilization Techniques, Boucher, American Journal Of Hospital Pharmacy, 29:660–672, (Aug.) 1972.

*Primary Examiner*—Robert J. Warden
*Assistant Examiner*—Krisanne M. Thornton
*Attorney, Agent, or Firm*—Hodgson, Russ, Andrews, Woods & Goodyear LLP

[57] ABSTRACT

A sterilization method and apparatus wherein microorganisms are exposed to ultraviolet light characterized by providing and operating a mercury/gallium metal halide ultraviolet light source in a manner exposing the microorganisms to ultraviolet light and a gaseous titanium dioxide emitted from the source for an exposure time in the range from about 0.3 seconds to about 60 seconds and at an exposure distance in the range from about 0.25 inch to about 4.0 inches, the ultraviolet light being emitted through a wavelength range from about 175 nanometers to about 450 nanometers with the relative energy being in the range from equal to or greater than 1.3 to equal to or less than 250 microwatts/sq.cm./nanometer at one meter. When the microorganisms are on the surface of an object, the surface is exposed to the ultraviolet light and to the titanium dioxide to provide a dynamic sterilization process on the surface so that the critical surface tension on the surface is changed and biological contaminant layers are actively removed from the surface without altering the originality of the surface which eliminates any shielding or screening of microorganisms on the surface and which provides complete sterilization on the surface with microcombustion of microorganisms. In addition, ozone-free quartz is provided in operative relation between the light source and the microorganisms.

9 Claims, 3 Drawing Sheets

STERILIZATION METHOD AND APPARATUS

CROSS REFERENCE TO A RELATED APPLICATION

This is a continuation of application Ser. No. 07/816,853 filed on Jan. 2, 1992 (abandoned) as a continuation of Ser. No. 07/257,444 filed Oct. 17, 1988 (abandoned) which was filed as a continuation-in-part of Ser. No. 07/112,504 filed Oct. 22, 1987 (abandoned).

BACKGROUND OF THE INVENTION

This invention relates to the art of sterilization, and more particularly to a new and improved sterilization method and apparatus employing ultraviolet light.

Traditionally, ultraviolet sterilization or germicidal radiation is accomplished by the passage of an electrical discharge through a low pressure mercury vapor and emitted at the 253.7 nanometer range. At this range, ultraviolet light has the ability to inactivate microbial forms. The amount of ultraviolet energy required to kill microorganisms is the product of time and intensity and is measured in microwatt seconds per square centimeter. Laboratory studies indicate that 8,000 microwatt seconds per square centimeter is sufficient for a 90 percent inactivation of most viruses and bacteria. Surviving microorganisms are left in a weakened state, interfering with replication and increasing their susceptibility to other inactivation methods including heat. This may be termed a static sterilization method, meaning only the microorganisms in direct reception of the ultraviolet light on the material surface are inactivated. Viruses and bacteria shielded by a continuously forming oxide layer, commonly associated with commercially pure titanium and titanium alloy instrumentation and implants, remain active. This microorganism protection from ultraviolet light is traditionally called a "screening effect". In addition to oxide layers, agglomerates, serum, blood, or even other cells may produce the shield, shadow zone, or screen effect. Thus, sterilization, using ultraviolet light in the traditional method, is very limited and unreliable in clinical application.

In recent times the phenomenon of surface energy activation has been the subject of various studies. These have involved examining biological films on material surfaces and their relationship to bioadhesion or biocompatability. Bioadhesion is essential to a successful osseointegrated bone implant. Studies over the years have encompassed sterilization, contaminants, critical surface tension, and the radio frequency glow discharge apparatus. Briefly findings from those studies are: bioadhesion is enhanced by a clean or surface energized" and sterilized material surface. Clean or "surface energized" means that a material surface is free of contaminants, agglomerates, and any oxide layer. Hence, the metal or material surface is bare or naked and very reactive to the surrounding environment.

Radio frequency glow discharge apparatus has been utilized in experiments for study of surface energy activation. The material's critical surface tension is changed thereby making it surface energy activated. To accomplish this surface energy activation on a specimen, the treatment requires the impact removal of an contaminant layers by the violently moving ionized gas particles within a chamber, and/or the microcombustion leading to complete conversion of the detached and contaminant layer matter to a gaseous form which is evacuated through a chamber exhaust. Two important points must be noted with respect to radio frequency glow discharge. First, surface energy activation or cleaning a material surface does not mean sterilization. Second, the material surface originality should not be changed, altered, or destroyed.

It would, therefore, be highly desirable to provide an ultraviolet sterilization method and apparatus which provides dynamic sterilization of a material surface and an increase in the critical surface tension of the material surface thereby inducing surface energy and increased bioadhesion.

SUMMARY OF THE INVENTION

It is, therefore, a primary object of this invention to provide a new and improved sterilization method and apparatus employing ultraviolet light which achieves a degree of sterilization heretofore unavailable with traditional ultraviolet techniques.

It is a further object of this invention to provide such a method wherein a complete single stage sterilization occurs on the material surface with the inclusion of microcombusting or ashing of microorganisms.

It is a further object of this invention to provide such a method wherein a dynamic sterilization process occurs on the material surface, eliminating any shielding or screening effect traditionally experienced by ultraviolet sterilization.

It is a further object of this invention to provide such a method wherein the critical surface tension will be changed, i.e. increased or decreased, on a material surface or specimen.

It is a further object of this invention to provide such a method wherein the biological contaminant layers, such as oxide layers, on a material surface or specimen, are actively removed without altering the material surface originality.

It is a further object of this invention to provide apparatus for carrying out a method which achieves the foregoing objects and which is relatively simple in construction and effective in operation.

The present invention provides a sterilization method and apparatus wherein microorganisms are exposed to ultraviolet light characterized by providing and operating a mercury/gallium metal halide ultraviolet light source in a manner exposing the microorganisms to ultraviolet light and a gaseous metal oxide emitted from the source for an exposure time in the range from about 0.3 seconds to about 60 seconds and at an exposure distance in the range from about 0.25 inch to about 4.0 inches, the ultraviolet light being emitted through a wavelength range from about 175 nanometers to about 450 nanometers with the relative energy being in the range from equal to or greater than about 1.3 to equal to or less than about 250 microwatts/sq. cm./nanometer at one meter. The gaseous metal oxide is titanium dioxide. When the microorganisms are on the surface of an object, the surface is exposed to the ultraviolet light and to the metal oxide, i.e. titanium dioxide, to provide a dynamic sterilization process on the surface so that the critical surface tension on the surface is changed and biological contaminant layers are actively removed from the surface without altering the originality of the surface which eliminate any shielding or screening of microorganisms on the surface and to provide complete sterilization on the surface with microcombusting of microorganisms. In addition, titanium-doped ozone-free quartz is provided in operative relation between the light source and the microorganisms.

The foregoing and additional advantages and characterizing features of the present invention will become clearly apparent upon a reading of the ensuing detailed description together with the included drawing wherein:

DETAILED DESCRIPTION OF THE ILLUSTRATED EMBODIMENT

Figure 1:
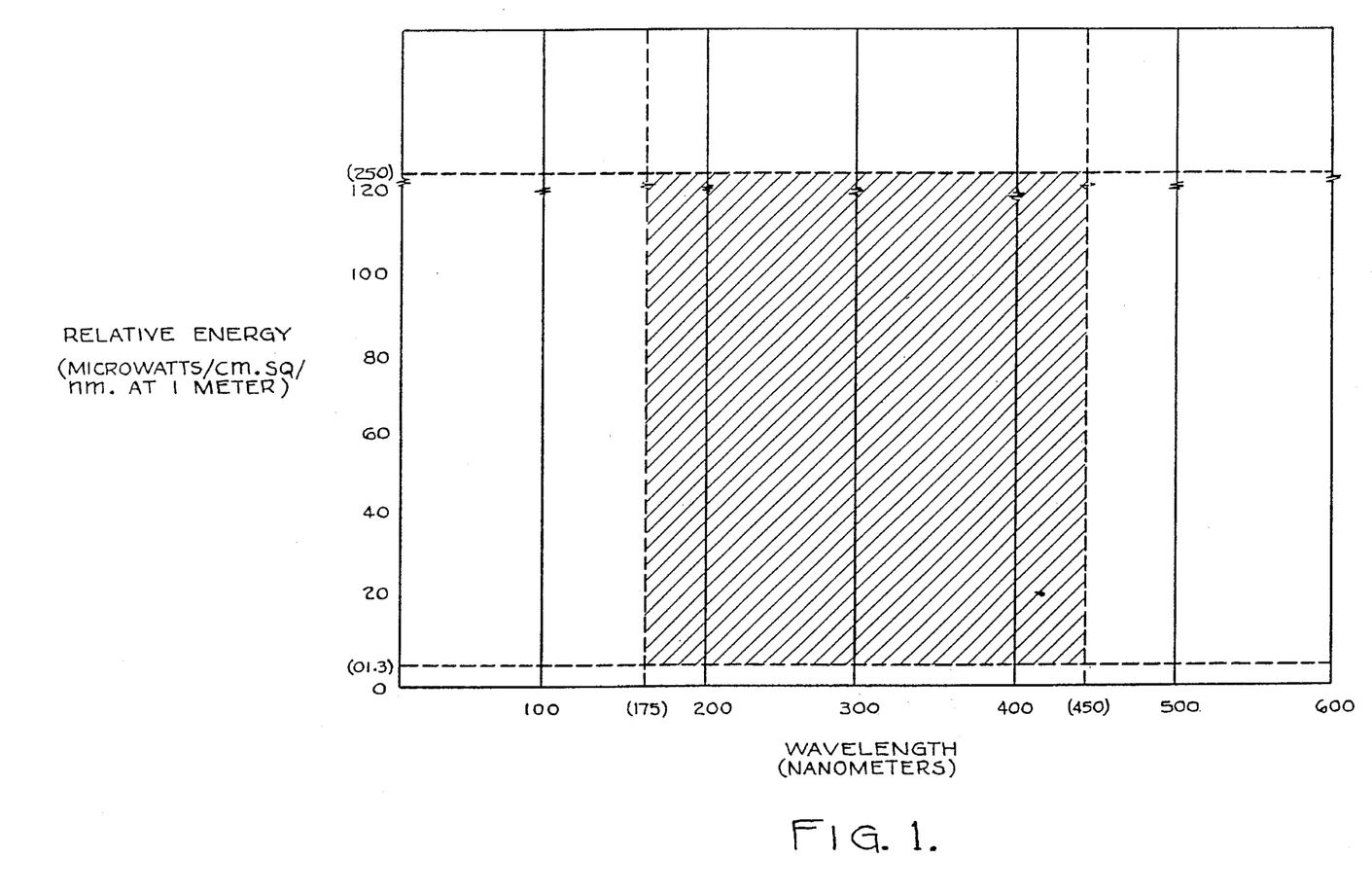
FIG. 1 is a graph of relative energy-wavelength range for sterilization and cleaning of material surface according to the present invention.

The ultraviolet sterilization method and apparatus of the present invention provides dynamic sterilization of a material surface and an increase in the critical surface tension of the material surface thereby inducing surface energy and increased bioadhesion. The dynamic sterilization combines ultraviolet light with molecular excitation. The process is accomplished by a metal halide mercury/gallium ultraviolet lamp, of ozone free quartz, with a wavelength output of about 175 through about 450 nanometers. From 175 through 450 nanometers, the range of relative energy must be equal to or greater than 1.3, or equal to or less than 250 microwatts/sq. cm./nanometer at one meter. The operative range of the metal halide mercury/gallium ultraviolet lamp which accomplishes the process is illustrated by the shaded area in FIG. 1 which is a graph of relative energy-wavelength range for sterilization and cleaning of material surface according to the present invention. To accomplish the process, the time of material surface exposure may vary from about 60 seconds to about 0.3 seconds. The time of material exposure is dependent on the relative energy, microwatt output of the lamp and the type of microorganisms to be destroyed. The distance between surface and the light source is in a proven range from about 0.25 to about 4.0 inches. The environmental or chamber temperature may vary between about 40 to about 150 degrees Centigrade within the previously stated distance range.

Figure 2A:
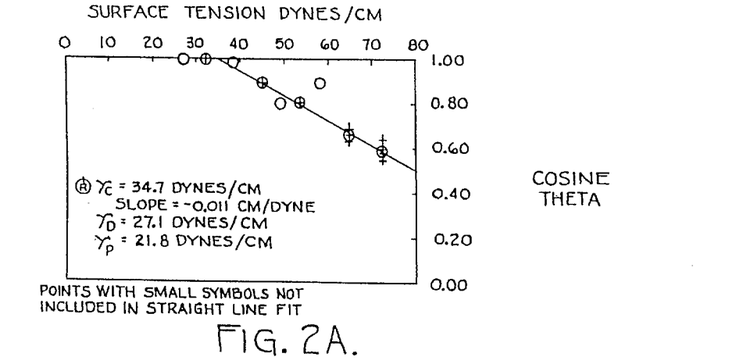
FIG. 2A is a Zisman plot of contact angle measurements for a pre-sterilized sample and FIGS. 2B–2F are Zisman plots of contact angle measurements on the sample treated by various methods including the method of the present invention.
Figure 2B:
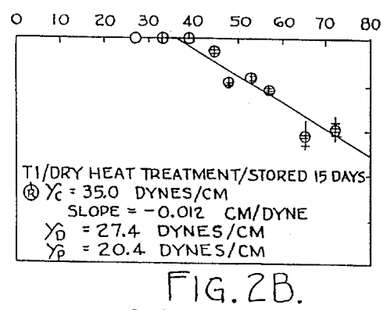
Figure 2C:
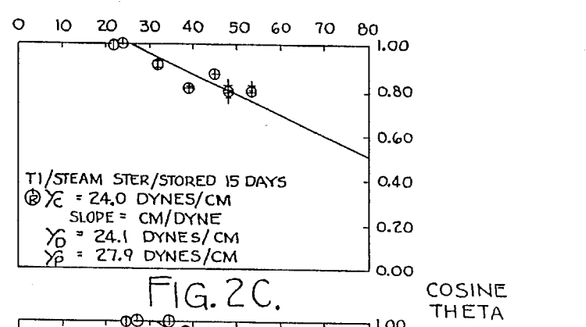
Figure 2D:
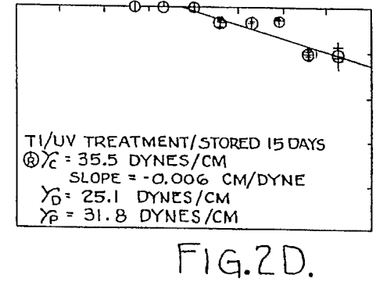
Figure 2E:
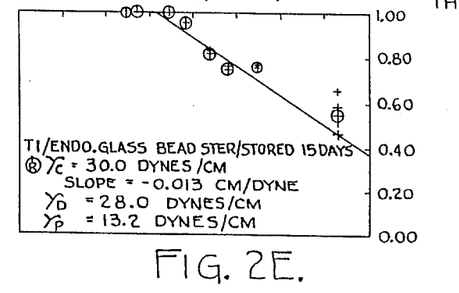
Figure 2F:
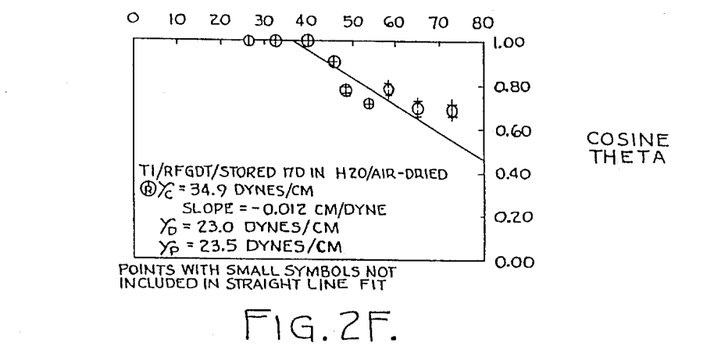

A mercury/gallium metal halide ultraviolet lamp, of the high energy output parameters described hereinabove and having an envelope of titanium-doped ozone free quartz, emits gaseous titanium dioxide. This will be described in further detail presently. With this emission, in addition to the ultraviolet light in the 350 to 450 nanometer wavelength range in an enclosed chamber, the process of surface energy activation occurs. Test have proven that the critical surface energy of the specimen is increased, thereby increasing the bioadhesiveness or biocompatibility. For a more detailed description of such tests and results thereof, reference may be made to "Surface Analysis Of Titanium Following Sterilization—Role In Implant-Tissue Interface and Bioadhesion", James H Doundoulakis, *Roswell Park Memorial Institute Annual Research Report*, 1986, the disclosure of which is hereby incorporated by reference. Briefly, as described in more detail in that report, FIG. 2A is a Zisman plot of contact angle measurements for a pre-sterilized titanium sample and FIGS. 2B–2F are Zisman plots of contact angle measurements on the sample sterilized by the following methods: dry heat treatment, steam sterilization, ultraviolet according to the present invention, endodontic glass bead sterilization and radio-frequency glow discharge, respectively. The plot for the method of the present invention, FIG. 2D, shows a high P and shallow slope confirming a potential for strong biologic reactivity.

The germicidal energy required to destroy common microorganisms including bacteria, viruses and spores, i.e. sterilization, is given in micro (u) Joules (J) per sq. cm. or work per area. The work (J) is the product of energy in watts (w) times time in seconds (sec.). Thus:

1 uJ=1 uw×1 sec.

or 1 uJ/sq. cm.=1 uw-sec./sq. cm.

Sterilization occurs at a wavelength of 253.7 nanometers. At 253.7 nanometers (nm.) wavelength, the ultraviolet lamp described produces about 14.146 uw/sq. cm./nm. at 1 meter. If the relative energy at 253.7 nm. is 14.146 uw/sq. cm., then in 9.7641 sec. MPET (maximum permissible exposure time for the above-described lamp), the work per area is 138.123 u w-sec./sq.cm. It is noted that 8,000 u w-sec./sq. cm. is needed to destroy most microorganisms according to traditional sterilization techniques using conventional mercury germicidal lamps. The foregoing is described in further detail in the above-noted Report by Doundoulakis which combined the ultraviolet energy at 253.7 nanometers with the surface molecular excitation and microcombustion. Traditional ultraviolet sources lack the capacity to penetrate and cause molecular excitation by photon energy. The dynamic sterilization provided by the present invention is capable of penetrating and causing excitation of molecules on the surface, therefore not requiring the amount of energy commonly associated with traditional ultraviolet methods. The excitation phenomenon in dynamic sterilization is similar to sputtering and involves the movement of superficial molecular particles. During this process large quantities of thermal energy are released, resulting in microcombustion of any unstable surface debri.

By combining the activity involved with the surface energy activation process simultaneously with the ultraviolet static light germicidal energy at 253.7 nanometers, the previously described phenomenon of shielding or screening effect is eliminated. In addition, the microcombustion occurring during the surface energy activation inactivates or, in histological terms, "ashes" any microorganisms surviving the 253.7 nanometer ultraviolet wavelength. The 350–450 nanometer ultraviolet light is believed to perform the ashing. Hence, there is an active or dynamic process occurring on the material surface during sterilization according to the present invention. This dynamic process facilitates complete sterilization without altering or injuring, either physically or chemically, the originality of the material surface. A prime example of this sterilization process is that a medical instrument with a sharp cutting edge such as a scalpel can be sterilized completely without injuring or dulling the instrument's cutting edge.

Figure 3:
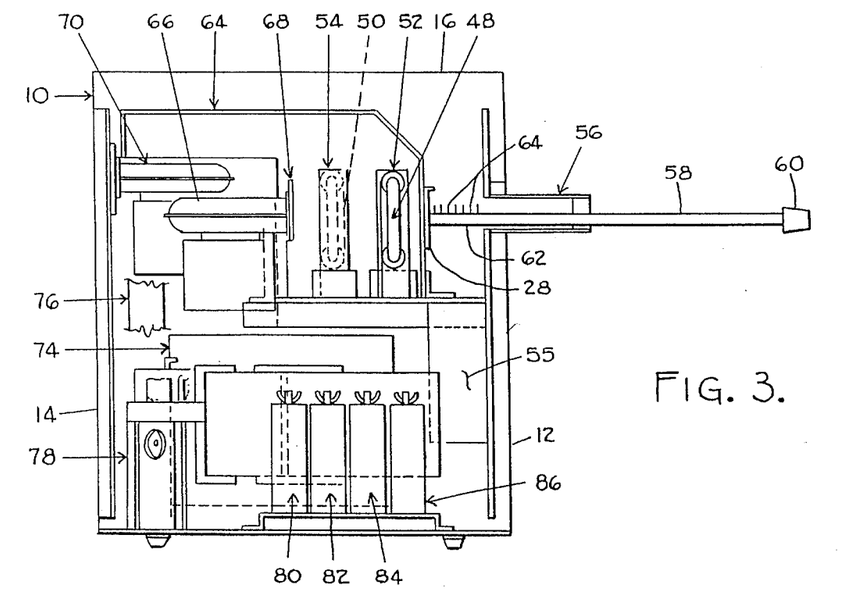
FIG. 3 is a side elevational view with parts removed of apparatus for carrying out the method of the present invention.
Figure 4:
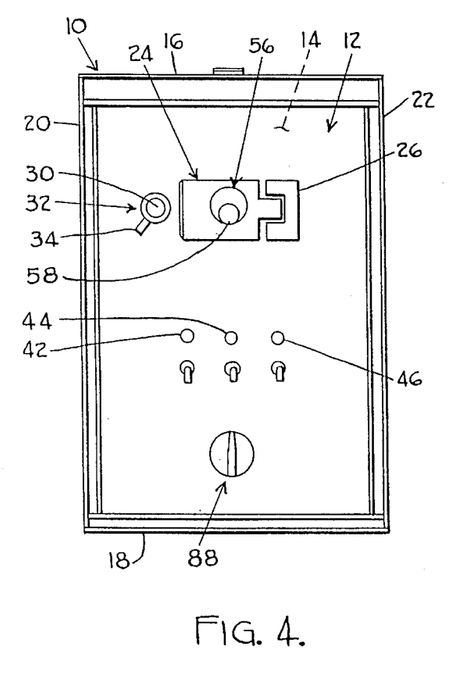
FIG. 4 is an end elevational view of the apparatus of FIG. 3.
Figure 5:
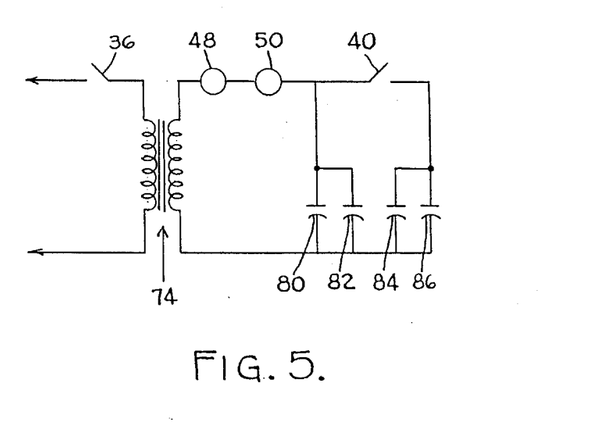
FIG. 5 is a schematic diagram of an electrical circuit included in the apparatus of FIGS. 3 and 4.

Apparatus for carrying out the method of the present invention is illustrated in FIGS. 3–5. The apparatus includes a housing or case 10 which can be generally rectangular in shape having front and rear panels 12 and 14, respectively, top and bottom panels 16 and 18, respectively, and side panels 20 and 22. A gate assembly 24 is pivotally connected to a bracket 26 mounted on the front panel 12. A shutter member 28 within housing 10 is fixed on one end of a rod 30 rotatably mounted in front panel 12 and provided with a knob 32 on the outer end which, in turn, includes a locking finger or tab 34 adapted to engage the gate assembly 24 when knob 32 is rotated to a locking position. Panel 12 also is provided with three manually-operated switches: a lamp switch 36, a power switch 38 and a surface energy activation (s.e.a.) switch 40. Corresponding indicator lamps 42, 44 and 46 show when the various switches are on.

The apparatus of this invention includes two identical lamps 48 and 50, each being a mercury/gallium metal halide ultraviolet lamp with titanium-doped ozone free quartz envelope. Each lamp 48,50 is of U shape or configuration, and lamps 48 and 50 are mounted in brackets 52 and 54 which, in turn, are supported on another mounting bracket assembly 55 secured in housing 10. Lamps 48,50 are in axially or longitudinally spaced relation, oriented with the legs in opposite directions, and disposed in generally parallel spaced apart planes. As a result, objects to be sterilized can be placed within and along both lamps, and the arrangement of the two U shaped lamps provides a substantially full circular exposure on objects such as implants.

The apparatus further comprises a specimen slide assembly including a tube 56 fixed in gate assembly 24, a rod 58 slidable within tube 56 provided with a knob 60 on the outer end, and a specimen holder or tray 62 carried by rod 58. Tray 62 can be provided with upstanding pins 64 to facilitate holding objects to be sterilized. When shutter 28 is pivoted to an open position, tray 62 can be moved by rod 58 to the left as viewed in FIG. 3 placing tray 62 and objects therein within the region bounded by lamps 48,50.

A reflector 64 is included within housing 10 and surrounding the lamps 48,50 to provide added protection for persons using the apparatus. A first fan 66 supported on bracket 68 is provided for cooling lamps 48,50 and a second fan 70 supported on bracket 72 is provided for exhausting air from housing 10. The apparatus also includes a transformer 74, terminal block assembly 76, relay 78 for controlling the force and a bank of four capacitors 80,82,84 and 86 for a purpose to be described. A timer (not shown) is controlled by a knob 88 on front panel 12.

FIG. 5 is a schematic circuit diagram illustrating the connection of lamps 48,50, transformer 74, capacitors 80,82, 84 and 86, lamp switch 36 and s.e.a. switch 40. When lamp switch 36 is closed, the primary of step-up transformer 74 is connected to conventional line voltage for operation at 115 volts and 220 ampere input power. The voltage is increased through the step-up transformer 74 to activate the lamps 48,50, each being an 800 or 1500 nominal watt, 500 arc volt tubular metal halide ultraviolet lamp of process parameters indicated herein. The apparatus has an idle or stand-by mode to extend the lamp life. The idle mode is accomplished by the circuit of FIG. 5 through the bank or network of capacitors 80,82,84 and 86 together with s.e.a. switch 40. When switch 40 is open, only capacitors 80 and 82 are in the circuit with lamps 48,50 and this is the idle mode. When switch 40 is closed, all four capacitors 80,82,84 and 86 are in circuit with lamps 48,50 and this is the full operation or high mode. With the provision of the idle mode, no additional warm-up time is required to bring the lamps to full efficiency when s.e.a. switch 40 is closed to place the apparatus in the high mode. Power switch 38 is not shown in FIG. 5 and controls operation of fans 66 and 70.

In the apparatus illustrated in FIGS. 3–5 each lamp 48,50 is of U shape or horse shoe configuration and is of the type commercially available from GTE-Sylvania under the designation MP1500T4U/8M rated at 1500 watts. An alternative form of lamp is of straight or tubular configuration and commercially available from GTE-Sylvania under the designation MP1500 T4/8B. Lamps of this type are provided with titanium-doped quartz tubing of the type which transmits little or no radiation below 200 nanometers, i.e. ozone-free quartz. This is the ozone-generating region, and the reduced transmission in this region provided by the quartz tubing avoids potential hazards associated with ozone. In alternative apparatus arrangements, objects or substances to be sterilized can be located within a tube or conduit of ozone-free quartz and the lamp or lamps located outside of and/or around such tube or conduit. For example, fluid to be sterilized such as blood would be conveyed through such conduit. The gaseous titanium dioxide emitted during the process of the invention results from operating the lamp with ozone-free quartz in the atmosphere. In particular, the ozone-free quartz associated with the lamp is doped with titanium for purposes of clarity. It is known that ultraviolet lamps having envelopes of ozone fee quartz doped with titanium will emit titanium dioxide when operated in air. Operation in air is required to provide oxygen for oxide formation by combination with titanium released from the ozone free quartz when exposed to the ultraviolet light. The titanium dioxide is responsible for the excitation phenomemen in the dynamic sterilization characteristics of the present invention. The foregoing is an illustrative sequence of steps for operating the apparatus of FIGS. 3–5 to carry out the method of the present invention.

1. Chamber 10 is placed on a level, sturdy stand in upright position.
2. Set all switches 36,38,40 in off position and rotate knob 32 counterclockwise in FIG. 4 to place lock 34 in locked position (otherwise apparatus will not function) which places shutter 28 in open position.
3. Plug chamber 10 into 115 volt, 220 amp grounded receptacle.
4. Turn power switch 38 to ON to operate fans 66 and 70.
5. Turn s.e.a. switch 50 to HIGH to place all four capacitors in the circuit.
6. Turn lamp switch 36 to ON to apply power to transformer 74, lamps 48,50 and capacitors 80,82,84 and 86.
7. Allow initial warm up time for lamps of five minutes.
8. Turn s.e.a. switch 40 to LOW to place the apparatus in the idle mode.
9. Pull drawer or specimen holder out from the chamber by means of rod 58.
10. Turn door lock knob 32 clockwise in FIG. 4 to close shutter 28 and unlock door or gate 24. Then pivot door 24 to access specimen holder 62.
11. Place instrumentation, implants, or material to be sterilized on specimen holder 62.
12. Pivot door 24 to insert holder 62 into the chamber and turn door lock 32 to lock position (counter clockwise) which opens shutter 28 and locks door 24.
13. Turn s.e.a. switch 40 to HIGH.
14. Push drawer or specimen holder 62 into chamber using rod 58.
15. Allow 8 seconds for surface energy activation and sterilization of material.
16. Repeat steps 8 through 10 to remove sterilized objects.

By way of example, the foregoing procedure using the apparatus of FIGS. 3–5 was carried out for sterilizing three sample items: a titanium dental implant, a titanium medical instrument and a plastic surgical suture. First, the procedure was carried out on the previously described indicator to confirm sterilization capability of the method and apparatus. In particular, the indicator is of the type commercially available from Amsco Medical Products Division of American Sterilizer Company and is rated at 13,000 uw-sec./sq.cm. It is in the form of a vial containing a test medium, and the vial was placed in the chamber and the foregoing procedure carried out. Then the vial was removed and a test strip inserted therein into the medium. The test strip was removed from the vial and medium and incubated for about twenty four hours. Then it was compared to a color chart which indicated that the method and apparatus achieved the 13,000 energy level for sterilization. Then the procedure was carried out successively on the implant, instrument and suture. In each case, after the procedure, the specimen was investigated by spectrographic analysis and complete sterilization was confirmed. The relatively short exposure time of eight seconds is particularly advantageous in sterilizing plastic sutures. Conventional methods requiring considerably larger exposure times can melt or otherwise damage plastic sutures.

The present invention is further illustrated by the following additional example. In the first phase, designated Protocol A, sixty eight commercially pure titanium intraoral implants are utilized. The implants represented irregular shaped objects and their size offered intricacies which would produce "shadow zones". In particular, they are of the type commercially available from Bud Industries, Inc., Holland N.Y., and each has a threaded portion terminating at one end and having an annular flange at the opposite end. One half of them were fitted with closure plug as at the end adjacent the annular flange. All implants were further subdivided in four categories as indicated in the first row of Table I. Forty-eight implants fell into two equal subdivisions. In one area the implants with closure plugs and the other without. The remaining implants were also equally divided into two control subdivisions. Each control subdivision consisted of five implants with closure plugs and five without (total of 10 per subdivision). One subdivision is for positive control while the other for negative control.

All categories were ultrasonically cleaned for 20 minutes with residue free detergent as indicated in the second row of Table I and packaged for sterilization. The detergent employed was IMS from Hu-Friedy, Chicago, Ill. Sterilization, indicated in the third row of Table I, was accomplished in a Vernitron Regency autoclave. The cycle for sterilization is 20 minutes of exposure to moist heat at 120° C. and 15 psi. This preparation was to insure no contamination existed prior to inoculation.

TABLE I

Protocol A
68 Commercially Pure
Titanium Implants

| 10 Implants for Positive Control | 24 Implants With Closure Plugs | 24 Implants Without Closure Plugs | 10 Implants For Negative Control |
|---|---|---|---|
| Ultrasonic Cleaning for 20 min. | Ultrasonic Cleaning for 20 min. | Ultrasonic Cleaning for 20 min. | Ultrasonic Cleaning for 20 min. |
| Autoclaved to Sterlize | Autoclaved to Sterilize | Autoclaved to Sterilize | Autoclaved to Sterilize |

TABLE I-continued

Protocol A
68 Commercially Pure
Titanium Implants

| Random Inoculation with Spores of Bacillus Stearthermophilus | Inoculated with Spores Bacillus Stearthermophilus | Inoculated with Spores Bacillus Stearthermophilus | Exposed to Air In Sterile Petri Dish |
|---|---|---|---|
| | UV Treatment | UV Treatment | |
| | Placed In Trypticase Soy Broth and Incubated for 48 hrs at 56° C. | | |
| | Subcultured On Tryptocase Agar Enriched with 5% Sheep Blood | | |

The biological indicator deployed is Bacillus Stearthermophilus spores. This organism is gram negative aerobic rod bacteria. Its spores display the greatest resistance to heat and less sensitivity to radiation when compared to other microbes. This species is commonly recommended to access the validity of moist heat and ionizing radiation sterilization by the National Institute of Health. The spores were grown from a commercial biological indicator, in particular Attest Sterilization Monitoring by 3M Company, in five mls of trypticase soy broth commercially available from BBL Microbiology-Systems, Cockeysville, Md. and incubuated for one week at 56° C. This allowed the bacteria in the broth to reach a spore forming stationary phase for use as the inoculum.

Three implants with closure plugs were individually inoculated with a $10^6$ concentration of Bacillus stearthermophilus spores. Inoculum was limited to the top and threaded areas of the implant. This was done with a medium fine sterile camel hair artist's brush. The contaminated implants were placed on a sterile titanium tray such as specimen holder 62 in the apparatus of FIG. 3 so that the flange of the implant supported it in a vertical position. They were exposed to 2537Å UV treatment in the apparatus of FIGS. 3 and 4 which was confirmed by a BLAK-RAY Ultraviolet meter to measure short wave intensities. The first exposure lasted 10 seconds, then the implants were turned upside down into another sterile titanium tray and again exposed for 10 seconds. The manipulation of implants was done with sterile forceps. The next trial utilized implants without closure plugs. These were inoculated in the same manner and placed on posts. The initial exposure in the apparatus was for 10 seconds before transferring them onto the sterile titanium tray for the second exposure. Each category was alternated until 18 trials, with 3 implants per trial, were finished. Once the desired exposure was established after each trial, every implant was placed in 5 mls Trypticase soy broth (one implant per test tube) and incubuted for 48 hrs. at 56° C. The test tube with broth and implant were evaluated for turbity implicating a failure in sterilization. The foregoing is set forth in Table I.

During the length of the experiment ten implants were inoculated in the same manner individually ten different times to indicate a positive control. Also a number of implants were used for a negative control. These however were placed in sterile petri dishes for one minute duration and exposed to conditions of the room. This was done 10 times to see if any outside contaminents entered the experiment. Again all positive and negative control implants were placed in the trypticase soy broth and incubated similarly.

Twenty four hours later all test tubes were subcultured onto a trypticase agar medium enrichted with 5% sheep blood commercially available from BBL Microbiology Systems Cockeysville, Md. This was not done for the positive controls. The subcultures were incubated for seven days at 56° C. to verify that the initial growth medium was adequate.

Sterility was maintained strictly during the entire experiment.

For the next phase, designated Protocol B, five commercially pure titanium implants were prepared identically as in Protocol A. Again inoculation was done with a sterile brush, however, these implants were allowed to dry for one hour before subjecting theme to Scanning Electron Microscope inspection. After S.E.M. examination, the contaminated implants were reinoculated to insure no interference from the electron beam in the S.E.M. is evidenced. Ultraviolet exposure was for 10 seconds initially, followed by appropriate manipulation to expose the underside for another 10 seconds. This was followed by placement into the Trypticase soy broth after treatment and incubuated for 48 hours at 56° C. Once the results of sterility were noted these implants were retrieved for a 2nd examination under S.E.M. The foregoing is illustrated in Table II. Again sterility was maintained during the entire procedure.

TABLE II

Protocol B

5 Commercially Pure
Titanium Implants Without Closure Plugs
Pretreated and Sterilized
as In Protocol A
Inoculated With
Spores of *Bacillus Stearthemophilus*
Scanning Electron
Microscope Examination
Reinoculated
UV Treatment
Placed in Trypticase Soy
Broth and Incubated
for 48 hrs. at 56° C.
Second SEM
Examination The results obtained from Protocol A for titanium implants after contamination with spores from the species *Bacillus stearthermophilus* followed by UV treatment, prove its effectivness in sterilizing irregular shaped objects. Only one of the 48 implants had failed to meet criteria for verifying sterilization as evidenced by turbidity of broth indicating microbial growth. The results from the experiment were determined by comparing turbidity in the growth medium to the individual results of the positive and negative controls. In addition, turbidity present in the positive controls indicated that viable organisms were present during inoculation. The negative controls provided that no contamination from the environment entered the experiment. In particular, the negative controls remained clear when compared to the unutilized broth. Raw data analysis shows that 96% of the implants with closure plugs had been sterilized and 100% of the implants without closure plugs were successfully sterilized as indicated by lack of turbidity in the broth. These percentages imply that "shadow zones" created by irregular shaped objects did not have a tremendous effect on the outcome.

The subcultures which were done 24 hours later did confirm identical results to the trypticase soy broth. The enriched growth medium did not aid in producing colonies except for the implant which had failed. Therefore, no interference was noted due to the initial growth media used.

Table III shows the temperature variations in the room and ultraviolet (UV) chamber. At the start of the experiment the UV chamber temp was 90° C. and when the trials completed it was 100° C. During each trial the temperature of UV chamber only increased by 10° C. with every 10 second exposure. No significant temperature increases were noted unless the UV apparatus was allowed to run indefinitely.

The implant which had failed sterilization was treated in the first trial. The two other implants of the same trial had been successfully sterilized. The implant which failed was known to be inadvertently contacted with a contaminated surface during transfer from the sterilization chamber to the test tube.

The results from protocol B were investigated by Scanning Electron Microscope Inspection. This protocol was devised to confirm that the inoculum had spores present and they were mixed in with debri from dead vegatative cells. Under S.E.M. inspection of an individual thread on the implants revealed inoculation debri with spores and also a defect in the thread from the milling process. By increasing the S.E.M. magnification it was evident that spores were present and well distributed around the defect. UV treatment again sterilized all five of the implants by not producing trubidity in the trypticase soy broth. The implant was reexamined by S.E.M. after sterilization and the defect was observed to be free of debri and spores. This finding supports the fact that "screening effects" by microimperfections and debris did not influence the outcome of the experiment.

TABLE III

Temperatures At Various
Stages of UV Treatment

| START - (Following 20 Min. Chamber Warm Up) | |
|---|---|
| Room | Chamber (Lamp on High for 1 Min. 45 Sec |
| 72° F. | 193° F. |
| 24° C. | 90° C. |

| FINISH | |
|---|---|
| Room | Chamber |
| | a) After 1 Min Warm Up On High |
| 70° F. | 212° F. |
| 22° C. | 100° C. |
| | b) After 10 Sec. Exposure |
| | 230° F. |
| | 110° C. |

Note: Bulb will not run beyond 250° C. 475° F.

The foregoing supports the following conclusions. Dynamic sterilization with ultraviolet light posseses the potential to irradiate all surfaces of the irregular shaped objects thus eliminating "shadow zones" and "screening effects" created during use of traditional ultraviolet light. Dynamic sterilization is a rapid and convenient method of destroying biological indicator spores, which supports the capabilities of ultraviolet light for sterilization. Dynamic sterilization should be utilized to sterilize titanium implants since it also produces controlled surface properties necessary for osseointegration.

The method and apparatus of the present invention advantageously eliminates any shielding or screening effect traditionally experienced by conventional ultraviolet sterilization and thereby achieves higher degrees of sterilization. In particular, the method and apparatus of the present invention employs dynamic sterilization by which ultraviolet light penetrates and excites molecules on the surface of an object thereby releasing thermal energy. As a result, all surface debris, including bacteria, viruses and spores, is vaporized, without causing damage or erosion to the sterilized object. Other sterilization devices, such as the autoclave, involve a combination of heat, pressure or steam which dulls and wears down an object's surface over time. Another limitation of such conventional approaches is that they sterilize, but do not vaporize, the foreign matter. As compared to radio frequency glow discharge, the method of the present invention has a number of advantages. With radio frequency glow discharge, process time typically is about twenty minutes, a vacuum chamber with argon gas is required and the surface being sterilized is not only cleaned but also textured. With the present invention, process time is a maximum of about one minute and often considerably shorter, it is carried out in a standard or normal atmosphere and it cleans but does not destroy the original surface. The process of the present invention achieves sterilization at an ultraviolet wavelength of 253.7 nanometers, but no comparable sterilization data is available for radio frequency glow discharge.

The method and apparatus of the present invention finds advantageous use in a wide variety of applications. As indicated in the foregoing examples, by successfully destroying biological indicator spores, it is particularly useful in sterilizing irregular shaped objects, especially titanium implants. In particular, the method and apparatus of the present invention provides sterilization of the implant surface, removal of all organic debris from the surface of the implant thereby providing an exceptionally clean surface and production of a high critical surface tension and, therefore, a high surface energy measured at between 40 and 70 dynes/cm. The significance of these results in addition to the cleaning and sterilization features, is the high surface energy produced by ultraviolet light treatment which enhanced and promoted tissue adhesion or tissue acceptance, known as osseointegration of implant devices which is so critical in oral and maxillofacial implants, orthopedic implants and spinal fixation devices, in order to improve clinical success rates under function. The ultraviolet light chamber apparatus of the present invention with its unique features of sterilization and cleaning in 8 to 10 seconds, with minimal heat, at chairside, therefore available for immediate use in patients, can have a major, positive impact on the needs of the medical, dental and allied health professions.

Since the method and apparatus of the present invention sterilizes and cleans without the use of water or high heat, utilization of the invention also has potential application in such areas as the maintenance of sharp edges and prevention of rusting and corrosion of surgical instruments, as well as resterilization of suture material without a loss of fiber strength. The method and apparatus of the present invention also has the capability of cleaning surfaces of small titanium valves, small-sized electronic components and other small metal and plastic parts to remove unwanted contaminants which could otherwise interfere with operation of such parts. The capability of cleaning items of plastic material such as sutures can be extended to plastic containers and packages thereby providing application of the method and apparatus of the present invention in food processing and food handling. As previously described, the method and apparatus also may find use in sterilizing fluids and liquids such as blood as possible treatment of minimal water and sewage.

It is therefore apparent that the present invention accomplishes its intended objects. There is provided an ultraviolet sterilization method and apparatus which provides dynamic sterilization of a material surface and an increase in the critical surface tension of the material surface thereby inducing surface energy and increased bioadhesion and which achieves a degree of sterilization heretofore unavailable with traditional ultraviolet techniques. In particular, the critical surface tension is changed (increased or decreased) on a material surface or specimen. The biological contaminant layers, such as oxide layers, on a material surface or specimen, are actively removed without altering the material surface originality. A dynamic sterilization process occurs on the material surface, eliminating any shielding or screening effect traditionally experienced by ultraviolet sterilization. A complete single stage sterilization occurs on the material surface with the inclusion of microcombusting or ashing microorganisms. The resulting induced surface energy and increased bioadhesion allows more immediate osseointegration thus expediting the healing phase of implantation.

While an embodiment of the present invention has been described in detail, that is for the purpose of illustration, not limitation.

I claim:

1. In a method of sterilizing a surface of an object wherein the nature of the surface is such that the critical surface tension is changeable and the physical and chemical originality of the surface is unalterable when exposed to high energy ultraviolet light and a metal oxide and wherein there is provided a mercury/gallium metal halide ultraviolet light source having an ozone-free metallic doped quartz envelope, the improvement comprising:

a) placing the object with the surface to be sterilized in proximity to said light source at a distance providing rapid heat transfer between said light source and said object and surface;

b) operating said light source to emit high energy ultraviolet light and a metal oxide, said ultraviolet light being emitted through a wavelength range from about 175 nanometers to about 450 nanometers;

c) exposing said surface to said ultraviolet light and to said metal oxide for a time sufficient to provide a dynamic sterilization process including irradiation by said ultraviolet light, sputtering by said metal oxide and said rapid heat transfer simultaneously on said surface so that the critical surface tension on said surface is changed and biological contaminant layers are actively removed from said surface without altering the originality of said surface which eliminates any shielding or screening of microorganisms on said surface and which provides complete sterilization on said surface with microcombusting of microorganisms; and d) wherein the portion of the energy of said ultraviolet light in the wavelength range from about 350 nanometers to about 450 nanometers provides said sputtering and the portion of the energy of said ultraviolet light in the wavelength range from about 175 nanometers to about 300 nanometers provides sterilization at about 253.7 nanometers.

2. A method according to claim 1, wherein said metal oxide is titanium oxide.

3. A method according to claim 1, wherein the range of relative energy of said ultraviolet light is between equal to or greater than 1.3 and equal to or less than 250 microwatts/sq. cm./nanometer at one meter.

4. A method according to claim 1 wherein the exposure time of said surface is in the range from about 0.3 seconds to about 60 seconds.

5. A method according to claim 1, wherein the distance between said light source and said surface is in the range from about 0.25 inch to about 4.0 inches.

6. A method according to claim 1, wherein said step of exposing said surface is carried out in a standard atmosphere.

7. A method according to claim 1, wherein said steps of exposing said surface is carried out in an enclosure under standard atmospheric conditions.

8. In a sterilization method wherein microorganisms are exposed to ultraviolet light and wherein there is provided an ultraviolet light source comprising a mercury/gallium metal halide lamp having an ozone-free metallic doped quartz envelope, the improvement comprising:

a) operating said lamp to expose microorganisms to ultraviolet light and titanium dioxide emitted from said lamp for an exposure time in the range from about 0.3 seconds to about 60 seconds and at an exposure distance in the range from about 0.25 inch to about 4.0 inches to provide rapid heat transfer between said light source and said microorganisms, the ultraviolet light being emitted through a wavelength range from about 175 nanometers to about 450 nanometers with the relative energy being in the range between equal to or greater than 1.3 and equal to or less than 250 microwatts/sq. cm./nanometers at one meter to provide dynamic sterilization including the simultaneous process of irradiation by said ultraviolet light, sputtering by said metal oxide and said rapid heat transfer; and b) wherein the portion of the energy of said ultraviolet light in the wavelength range from about 350 nanometers to about 450 nanometers provides said sputtering and the portion of the energy of said ultraviolet light in the wavelength range from about 175 nanometers to about 300 nanometers provides sterilization at about 253.7 nanometers.

9. The improvement according to claim 8, wherein said microorganisms are exposed to said ultraviolet light and titanium dioxide under standard atmospheric conditions.

* * * * *